(12) United States Patent  (10) Patent No.: US 7,322,944 B2
Osawa et al.  (45) Date of Patent: Jan. 29, 2008

(54) GUIDE WIRE

(75) Inventors: Shinji Osawa, Osaka (JP); Hidekazu Miyauchi, Osaka (JP)

(73) Assignee: Nipro Corporation, Osaka (JP)

( * ) Notice: Subject to any disclaimer, the term of this patent is extended or adjusted under 35 U.S.C. 154(b) by 76 days.

(21) Appl. No.: 10/825,422

(22) Filed: Apr. 16, 2004

(65) Prior Publication Data

US 2004/0210163 A1  Oct. 21, 2004

(30) Foreign Application Priority Data

Apr. 18, 2003 (JP) .............................. 2003-113847

(51) Int. Cl.
*A61B 5/00* (2006.01)
*A61M 25/00* (2006.01)

(52) U.S. Cl. ..................................... 600/585
(58) Field of Classification Search ............. 600/433, 600/434, 585; 604/164.01, 164.13
See application file for complete search history.

(56) References Cited

U.S. PATENT DOCUMENTS

| 4,538,622 A | 9/1985 | Samson et al. ............. 128/772 |
| 4,619,274 A | 10/1986 | Morrison ..................... 128/772 |
| 4,934,380 A * | 6/1990 | de Toledo ................... 600/585 |
| 5,103,543 A * | 4/1992 | Hodgson .................... 29/896.9 |
| 5,234,437 A * | 8/1993 | Sepetka ...................... 606/108 |
| 5,551,444 A | 9/1996 | Finlayson ................... 128/772 |
| 5,640,970 A * | 6/1997 | Arenas ........................ 600/585 |
| 5,833,631 A * | 11/1998 | Nguyen ...................... 600/585 |
| 5,951,496 A | 9/1999 | Willi .......................... 600/585 |
| 6,183,420 B1 | 2/2001 | Douk et al. ................. 600/462 |

FOREIGN PATENT DOCUMENTS

| EP | 0 318 046 A2 | 5/1989 |
| EP | 0 815 894 A1 | 1/1998 |
| JP | 4-25024 B2 | 4/1992 |
| JP | 6-327775 A | 11/1994 |
| JP | 8-243169 A | 9/1996 |
| JP | 2981976 B2 | 9/1999 |
| WO | 98/18516 A1 | 5/1998 |

* cited by examiner

*Primary Examiner*—Max F. Hindenburg
*Assistant Examiner*—Jonathan M Foreman
(74) *Attorney, Agent, or Firm*—Kubovcik & Kubovcik (57) ABSTRACT

A guide wire which includes: (a) a core wire formed with a mounting portion at the distal end portion; and (b) a plurality of coil wires being fitted onto the mounting portion substantially in tandem, and having different mechanical properties, the adjacent coil wires being connected with each other at the corresponding ends thereof. One of the corresponding ends of the adjacent coil wires is formed into a tapered portion gradually reducing in outer diameter toward said end. The other one of the corresponding ends is formed into a receiving end portion into which the tapered portion is inserted.

4 Claims, 8 Drawing Sheets

GUIDE WIRE

FIELD OF THE INVENTION

The present invention relates to a guide wire for introducing a catheter to a required portion of a human body for treatment or inspection.

DESCRIPTION OF THE RELATED ART

A catheter is used for a medical procedure such as a super selective angiography, a Percutaneous Transluminal Angioplasty (PTA), a Transcatheter Arterial Embolization (TAE), and a Percutaneous Transluminal Coronary Angioplasty (PTCA).

When introducing a catheter into the human body, for example, a guide wire for guiding the catheter is used in the following manner. In case of inserting the catheter into an artery for treatment or inspection, it is extremely difficult to insert the catheter since the pressure in the artery is higher than in a vein. Therefore, for example, a percutaneous catheter method (Seldinger method) is employed. In this method, a guide wire is first inserted into a blood vessel and indwelled there, and then a catheter is inserted into the blood vessel by fitting (laying) the catheter on the guide wire and advancing the same along the guide wire as an axis. With this method, a catheter can also be easily inserted into the artery.

A guide wire includes a core wire and a plurality of coil wires to be fitted at the distal end portion of the core wire in tandem (for example, see JP2981976B (page 3, and FIG. 1), JP4-25024B (pages 3-4, and FIGS. 1 and 2), JP6-327775A (page 4, column 5, and FIG. 1), JP8-243169A (page 5, column 8, and FIG. 1) and U.S. Pat. No. 4,619,274 (columns 3-4, and FIG. 2).

The core wire is formed of a flexible alloy and has (1) suitable flexibility having followability with respect to the blood vessel, and (2) rigidity capable of transmitting a rotational force or a pressing force to the distal side of the guide wire when operating the guide wire from the proximal side.

The plurality of the coil wires is formed of metallic material, and has flexibility capable being restored easily after deformation, and is superior in operability. In particular, the most distal coil wire is formed of (1) a material having lower rigidity than other coil wires so as to secure the flexibility and the adaptability at the distal side of the guide wire, and (2) a radiopaque material, that is, a material that can be photographed by radioactive rays so that the position can be tracked by radioactive rays.

In such a manner, the plurality of coil wires includes coil wires having different physical properties, such as a mechanical property, and these coil wires are connected to each other so as not to be displaced with respect to the core wire as will be described below.

For example, according to JP2981976B, wires constituting the respective coil wires are connected by a butt joint. However, with such joint, there is a problem in that the mechanical property such as hardness or tensile strength may suddenly change at the boundaries between two materials of different qualities. Therefore, in JP2981976B, wires thicker than the wire constituting the respective coil wires are prepared and welded with each other to form a single wire formed of different types of metals, and then the wire is drawn to draw the welded portions. Accordingly, the wire is provided with the mechanical properties that changes gradually at the welded portions and the peripheral portions thereof, and hence a sudden change in mechanical properties is prevented. Consequently, when the guide wire is bent at the distal side, the entire distal side is bent at a generally uniform radius of curvature, and no angular portion is generated on the bent portion. Therefore, problems (described later) found in the technologies disclosed in JP4-25024B, JP6-327775A, JP8-243169A, and U.S. Pat. No. 4,619,274 are avoided, and hence insertion into or retraction from a winding blood vessel or a branch blood vessel can be performed easily, and the possibility of damaging the wall of the blood vessel can be reduced.

In the technologies disclosed in JP4-25024B, JP6-327775A, JP8-243169A, and U.S. Pat. No. 4,619,274, the corresponding ends of the adjacent coil wires are connected in a screwed manner with respect to each other.

However, according to the technology disclosed in JP2981976B, since the wires formed of different types of metallic materials are welded and then drawn, the respective wires formed of the different types of metallic materials must have substantially the same level of tensile strength. Therefore, the type of the metallic material to be used is limited, and in particular, the metallic material for the coil wire at the distal side has also to be formed of a rigid metallic material, which causes a problem in flexibility and adaptability at the distal side of the guide wire.

In the technologies disclosed in JP4-25024B, JP6-327775A, JP8-243169A, and U.S. Pat. No. 4,619,274, there is no problem as in JP2981976B. However, since the corresponding ends of the adjacent coil wires are connected in a screwed manner with each other, or the adjacent coil wires are connected via a connecting coil wire screwed into these coil wires, there arises a problem in that the process of connecting them is troublesome, takes a lot of time, and cannot be performed easily.

In the technologies disclosed in JP4-25024B, JP6-327775A, JP8-243169A, and U.S. Pat. No. 4,619,274, since the adjacent coil wires are simply connected in a screwed manner as described above, the mechanical properties abruptly change at the connecting portions and the peripheral portions thereof. Therefore, when the distal side of the guide wire is bent, the entire distal side cannot be bent at a uniform radius of curvature, and hence the bent portions different in radius curvature continue, whereby the boundaries between the adjacent bent portions are angulated. Therefore, when the guide wire is inserted into a winding blood vessel, the angulated portions of the guide wire come into sliding contact with the wall of the blood vessel, and hence insertion into and retraction of the guide wire from the blood vessel are difficult, and there is a possibility of damaging the wall of the blood vessel. In addition, since the angulated portions of the guide wire interfere with a branched portion of the blood vessel, when the guide wire is inserted into the branch blood vessel, there arises a problem in that insertion of the guide wire into the branch blood vessel is difficult.

BRIEF SUMMARY OF THE INVENTION

As a result of earnest investigations made by the inventors to solve the problems associated with the conventional techniques, the invention has been completed.

It is an object of the present invention to provide a guide wire in which connection of the plurality of coil wires can be performed easily within a short time, and no problem in flexibility and adaptability is generated at the distal side of the guide wire.

The above-mentioned object and other objects of the present invention will be further clarified in the following description, and these objects are attained by the present invention comprising the constitution mentioned below.

The invention relates to a guide wire comprising:

(a) a core wire formed with a mounting portion at a distal end portion; and (b) a plurality of coil wires being fitted onto the mounting portion substantially in tandem, and having different mechanical properties, the adjacent coil wires being connected with each other at the corresponding ends thereof, wherein one of the corresponding ends of the adjacent coil wires is formed into a tapered portion gradually reducing in outer diameter toward said end, and wherein the other one of the corresponding ends is formed into a receiving end portion into which the tapered portion is inserted.

The mounting portion of the core wire may comprise:

(a) a plurality of transitional portions continuously disposed in the axial direction, and reduced gradually in outer diameter toward the distal end; and (b) a distal end portion continuously disposed distally from the most distal transitional portion, and formed into a plate shape, wherein the taper ratio of the most proximal transitional portion is larger than that of other transitional portions.

The coil wire positioned on the proximal side out of the adjacent coil wires may be formed with a tapered portion.

The pitches of the receiving end portion of the coil wire may be formed to be larger than those of the remaining portion thereof.

The length of the insertion of the tapered portion into the receiving end portion may be 2% to 40% of the whole length of the coil wire having a receiving end portion.

The most distal coil wire may be formed of a radiopaque material.

BRIEF DESCRIPTION OF THE DRAWINGS

FIGS. 1 and 2 show a first embodiment of the invention, and FIG. 1 is a side view.

FIGS. 3 and 4 show a second embodiment of the invention, and FIG. 3 is a side view.

FIGS. 5 and 6 show a third embodiment of the invention, and FIG. 5 is a side view.

FIGS. 7 and 8 show a comparative example, and FIG. 7 is a side view.

DETAILED DESCRIPTION OF THE INVENTION

Figure 1:
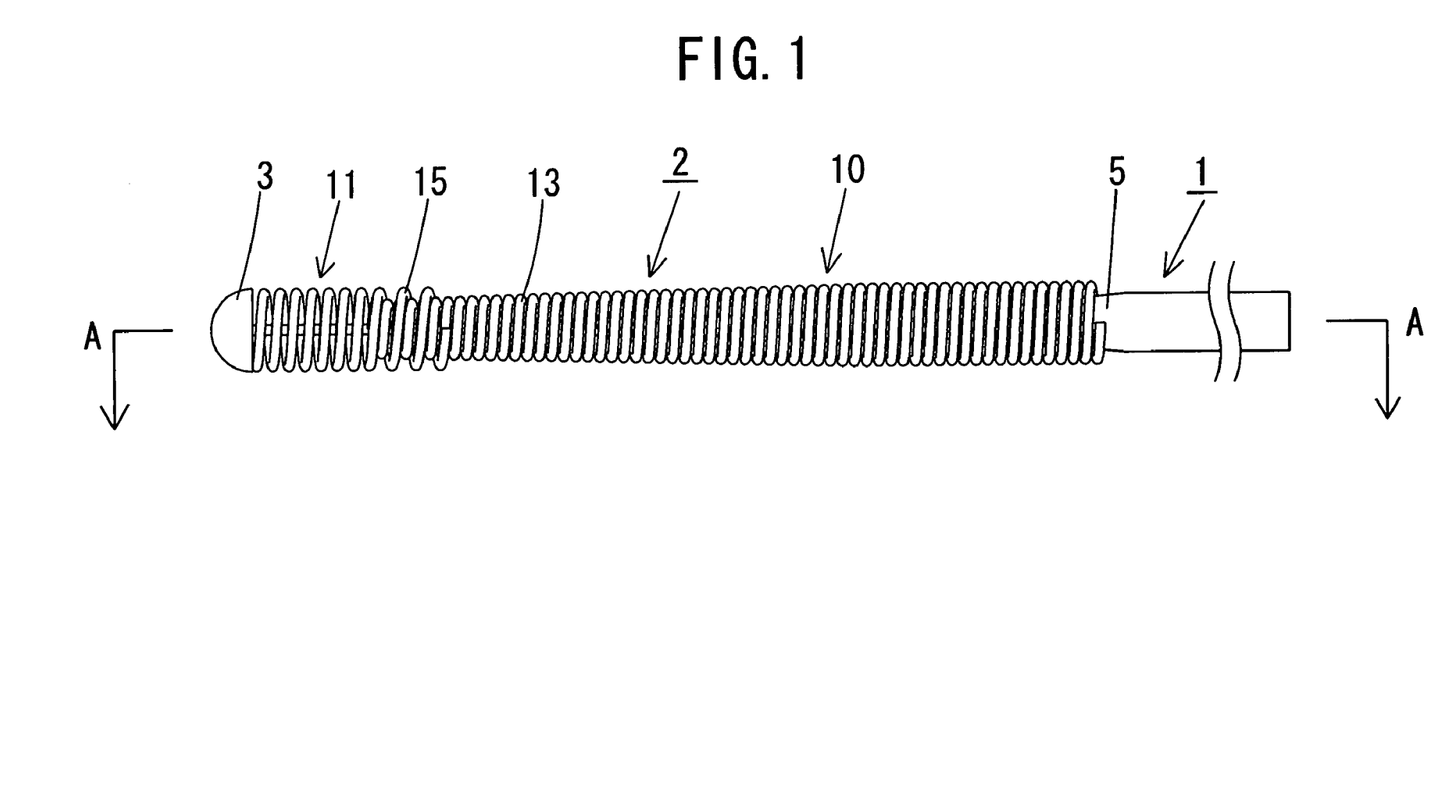
Figure 2:
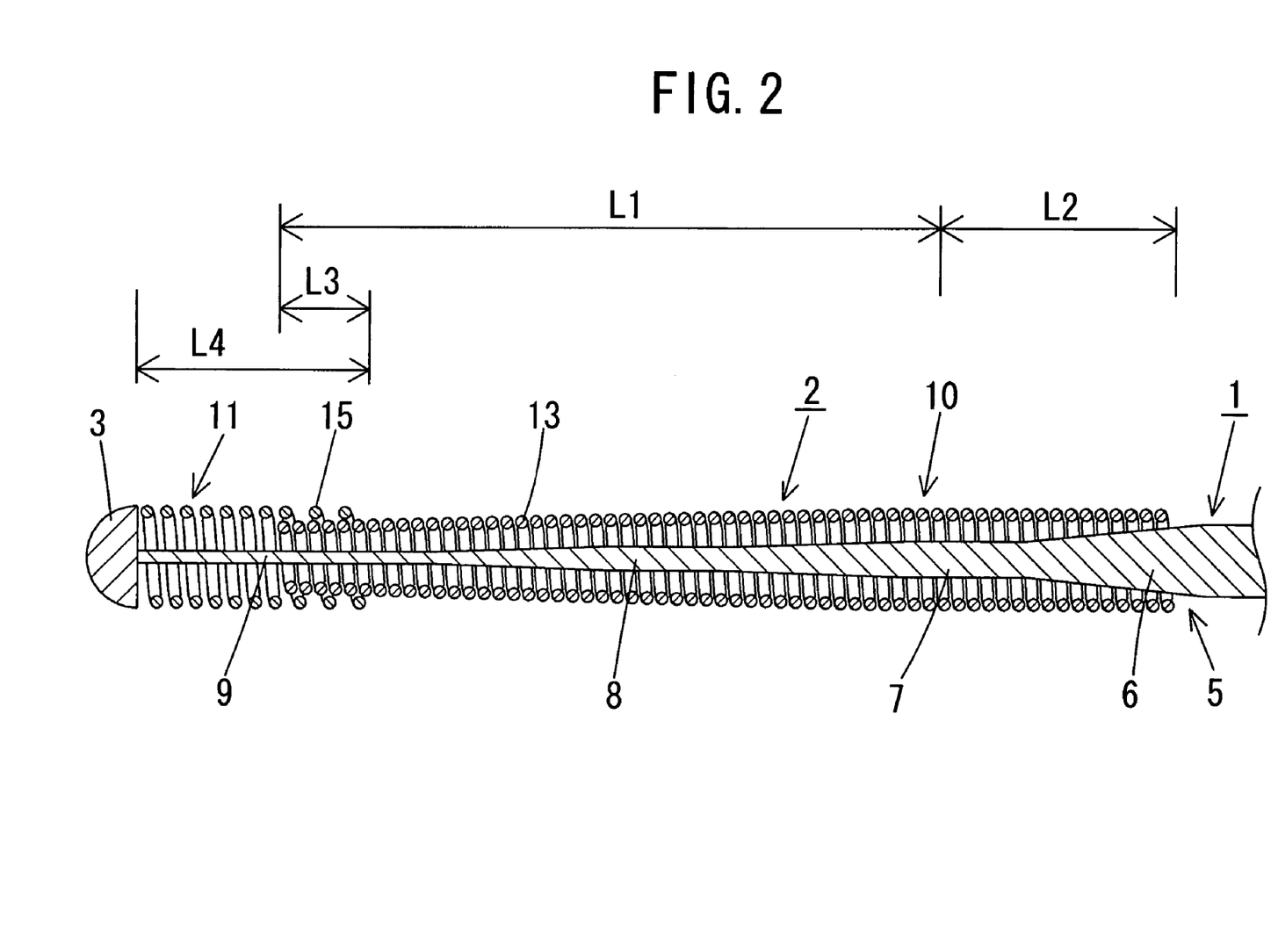
FIG. 2 is a cross-sectional view taken along line A-A of FIG. 1.

Referring now to FIGS. 1 and 2, a first embodiment of the present invention will be described. A guide wire includes a core wire 1, a coil wire assembly 2, and a distal end tip 3.

The core wire 1 has (1) adequate flexibility having followability with respect to the blood vessel, and (2) rigidity which enables transmission of a rotational force or pressing force to the distal end of the guide wire when operating the guide wire from the proximal side, and is formed of an elongated solid wire having flexibility and resiliency, and the distal end portion thereof is formed into a mounting portion 5 to which the coil wire assembly 2 is mounted. In order to improve the flexibility and the adaptability of the distal side of the core wire 1, the mounting portion 5 is configured by continuously disposing three transitional portions (tapered portions), that is, a proximal transitional portion 6, a center transitional portion 7 and a distal transitional portion 8, and a distal end portion (flat portion) 9 toward the distal end (front) in this sequence. The transitional portion may be provided in one location or in two locations or more, and preferably provided in two locations or more. Each of the transitional portions 6-8 is tapered in such a manner that the outer diameter is reduced toward the distal end, and the taper ratio of the proximal transitional portion 6 is larger than that of the center and the distal transitional portions 7, 8. The distal end portion 9 is formed into a thin-plate shape. The core wire 1 is integrally formed of a metallic material or a hard plastic material, and the outer surface is coated with a plastic material as needed. The metallic material used here is, for example, stainless steel, carbon steel, titan, beryllium copper, and nickel-titan alloy.

The coil wire assembly 2 includes two coil wires having different mechanical properties, that is, a proximal coil wire 10 and a distal coil wire 11, and the coil wires 10, 11 are fitted onto (mounted onto) the mounting portion 5 of the core wire 1 except for a proximal end portion of the mounting portion 5 substantially in tandem from the distal end. More specifically, the proximal coil wire 10 is fitted onto the transitional portions 6-8 and the distal end portion 9 of the mounting portion 5, and the distal coil wire 11 is fitted onto the distal end portion 9 of the mounting portion 5. The number of coil wires can be three or more. The outer surfaces of the respective coil wires 10, 11 are coated with a plastic material as needed, whereby friction drag between the guide wire and the catheter fitted thereon is reduced.

The whole length of the proximal coil wire 10 is longer than the whole length of the distal coil wire 11, and the portion of the proximal coil wire 10 except for the proximal portion is formed into a tapered portion 13 tapered in such a manner that the outer diameter (wound diameter) decreases toward the distal end, and the length L1 of the tapered portion 13 is longer than the length L2 of the portion of the proximal coil wire 10 other than the tapered portion 13. The proximal end portion of the proximal coil wire 10 is generally secured (fixed) to the proximal transitional portion 6 of the mounting portion 5 by brazing or soldering, but it may not be secured. The proximal coil wire 10 may be one tapered toward the distal end. The proximal coil wire 10 is integrally formed of a material, which is radiotransparent (high in X-rays transmissivity), that is, low in photographability by radioactive rays (X-rays) and high in resiliency. Included in such materials is, for example, austenitic stainless steel (for example, SUS316).

The hardness and the strength of the proximal coil wire 11 is adapted to be smaller than those of the proximal coil wire 10, and the rigidity is adapted to be lower than the proximal coil wire 10, so as to secure the flexibility and the adaptability of the guide wire at the distal side. The proximal end portion of the proximal coil wire 10 is formed into a receiving end portion 15 having larger (winding) pitches than the remaining portion. The distal end portion of the tapered portion 13 is inserted into the receiving end portion 15, and the both portions 13, 15 are secured and connected by brazing or soldering. The connection may be performed either before or after fitting the coil wires 10, 11 onto the core wire 1. The length L3 of the connected portion (the receiving end portion 15, or the insertion of the tapered portion 13 into the receiving end portion 15) is normally 2% to 40%, preferably, 2% to 17%, and more preferably 3% to 7% of tho whole length L4 of the distal coil wire 11. If it is below 2%, the connecting strength between the coil wires 10, 11 is not sufficient, and if it exceeds 40%, the flexibility and the adaptability of the distal coil wire 11 is deteriorated. The distal coil wire 11 is integrally formed of a material, which is radiopaque (low in X-rays transmissivity), that is, high in photographability by radioactive rays (X-rays). Accordingly, by utilizing radioactive rays such as X-rays, the position of the distal coil wire 11 can easily be observed from the outside of the body. Included in such materials is, for example, platinum-nickel alloy (for example, 90% of platinum and 7% of nickel).

Incidentally, the distal end of the proximal coil wire 10 may be formed to be the receiving end portion, and the proximal end of the distal coil wire 11 may be formed to be the tapered portion.

The distal end tip 3 is formed into a solid semi-spherical shape with its spherical surface being the distal end surface of the core wire 2, and is integrally formed of a metallic material. The distal end tip 3 is secured (fixed) to the respective distal ends of the distal end portion 9 of the core wire 1 and the distal coil wire 11 by brazing, soldering, or plasma jet welding after fitting the coil wire assembly 2 onto the mounting portion 5 of the core wire 1. Accordingly, the core wire 1 and the coil wire assembly 2 are integrally formed.

According to the embodiment described above, the coil wires 10, 11 are not connected in a screwed manner, but connected by inserting and securing the distal end of the proximal coil wire 10 in the receiving end portion 15, which is the proximal end portion, of the distal coil wire 11. Therefore, the work of connecting the coil wires can easily be performed within a short time. The type of the metallic material to be used for the coil wires 10, 11 is not limited, and in addition, it is not necessary to use a rigid metallic material for the distal coil wire 11. Therefore, it causes no problem in the flexibility and the adaptability of the distal side of the guide wire.

The proximal coil wire 10, which is connected to the distal coil wire 11, is formed to be larger in hardness and tensile strength, and higher in rigidity than the distal coil wire 11. But the portion of the proximal coil wire 10 except for the proximal portion thereof is formed into the tapered portion 13, the outer diameter of which reduces toward the distal end. Accordingly, the hardness and the tensile strength of the tapered portion 13 gradually decrease toward the distal end. Therefore, an abrupt change in mechanical properties such as hardness, tensile strength, and rigidity at the connecting portion of the coil wires 10, 11, and the portions of the coil wires 10, 11 adjacent to the connecting portion can be restricted (prevented). Accordingly, when the distal side of the guide wire is bent, the entire distal side is bent generally at a uniform radius of curvature, and an angulated portion is not generated at the bent portion. Accordingly, the (above-described) problems, which are found in the technologies disclosed in JP4-25024B, JP6-327775A, JP8-243169A, and U.S. Pat. No. 4,619,274, do not occur, whereby insertion into and retraction from the winding blood vessel or the branch blood vessel can be performed easily, and the possibility of giving damages to the wall of the blood vessel can be reduced.

Furthermore, with respect to the distal coil wire 11, the pitches of the receiving end portion 15 are adapted to be larger than that of the remaining portion, whereby the hardness and the tensile strength of the receiving end portion 15 are adapted to be smaller than those of the remaining portion, and the rigidity thereof is adapted to be smaller than the remaining portion. Accordingly, an increase in the combined tensile strength of the connecting portion of the coil wires 10, 11 and in the combined rigidity of those can be restrained (prevented). In addition, when the distal side of the guide wire is bent, the entire distal side is bent at a radius of curvature which is more uniform than the above-described one whereby insertion into and retraction from the winding blood vessel or the branch blood vessel can be performed easily, and the possibility of damaging the wall of the blood vessel can be further reduced.

In addition, since the distal side of the core wire 1, that is, the proximal portion of the mounting portion 5 to which the coil wire assembly 2 is mounted, is formed by providing three transitional portions 6-8 continuously disposed toward the distal end so that the outer diameter of the proximal portion gradually reduces toward the distal end, the flexibility and the adaptability of the mounting portion 5 can be gradually increased toward the distal end.

In addition, since the distal end portion 9 of the mounting portion 5 has a shape of a thin plate, the direction of bending of the distal end portion 9 is limited to the direction of the thickness thereof. Accordingly, insertion into and retraction from a winding blood vessel or a branch blood vessel can be performed easily.

Figure 3:
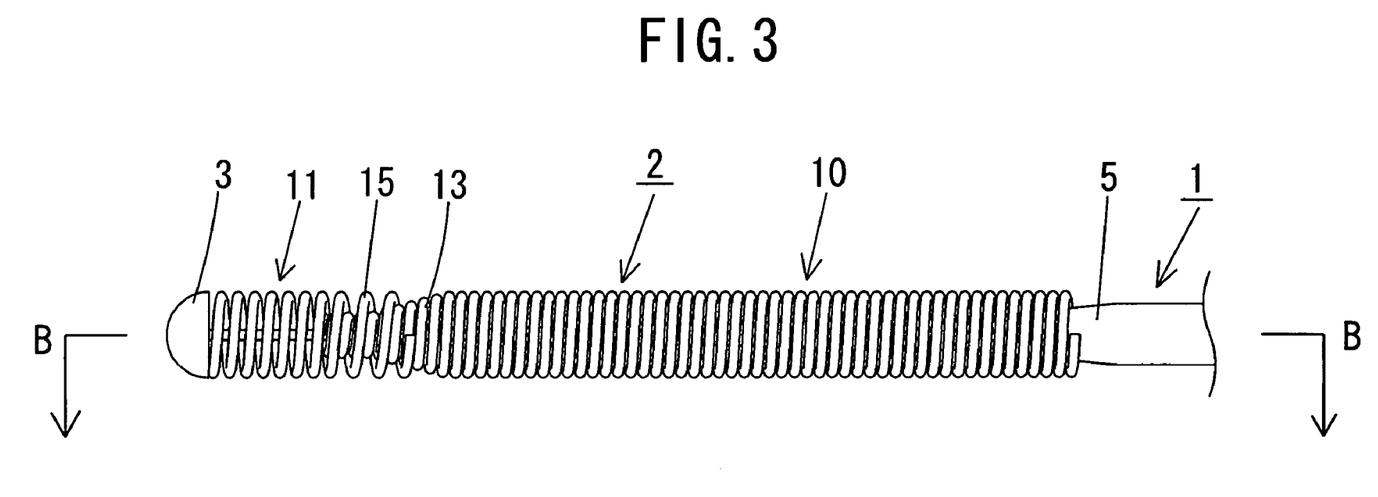
Figure 4:
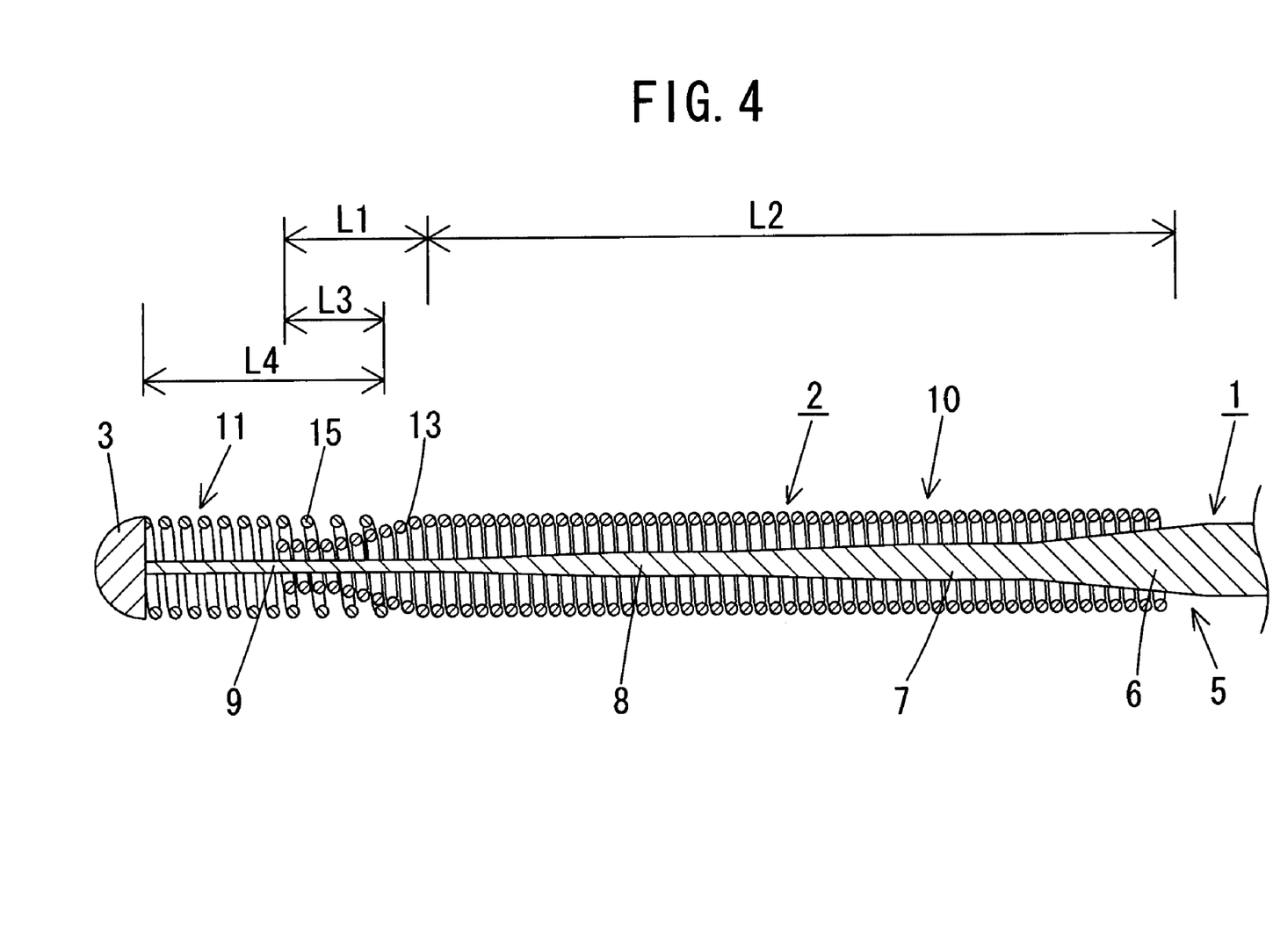
FIG. 4 is a cross-sectional view taken along line B-B of FIG. 3.

FIGS. 3 and 4 show a second embodiment of the present invention, which is a modification of the first embodiment. The length L1 of the tapered portion 13 of the proximal coil wire 10 is adapted to be shorter than the first embodiment, and the length L2 of the portion of the proximal coil wire 10 except for the tapered portion 13.

Figure 5:
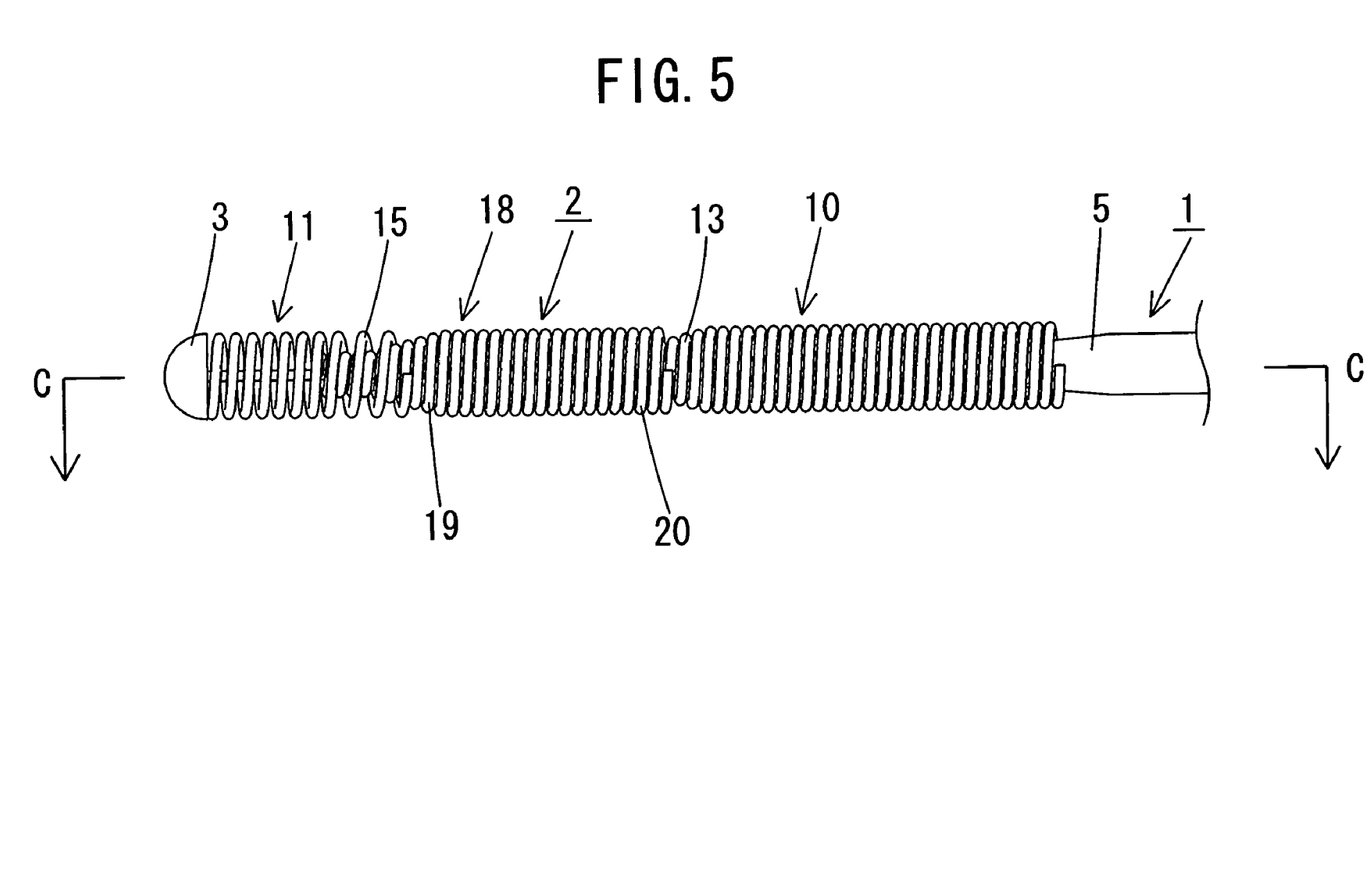
Figure 6:
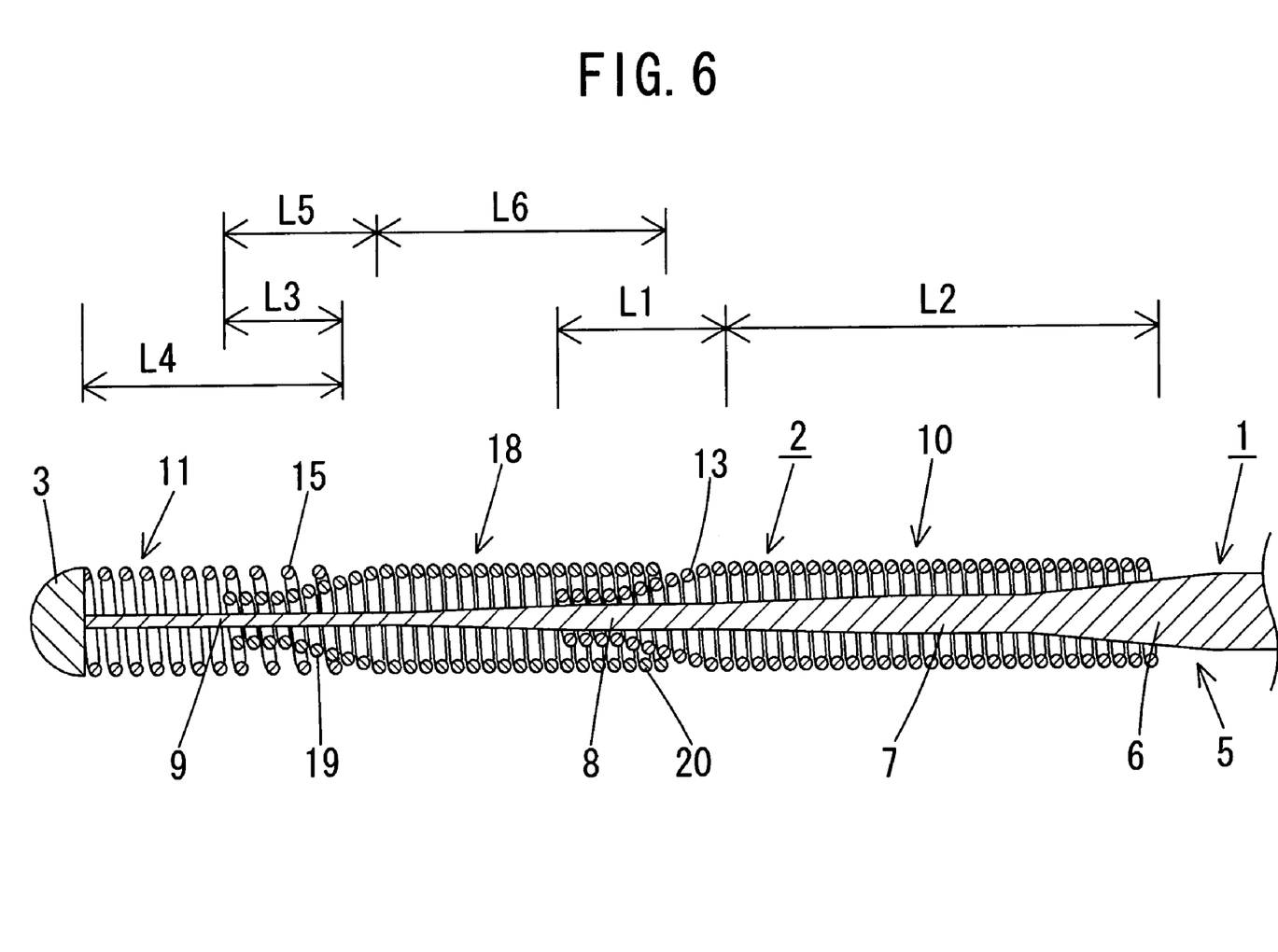
FIG. 6 is a cross-sectional view taken along line C-C of FIG. 5.

FIGS. 5 and 6 show a third embodiment of the present invention, in which the coil wire assembly 2 includes three coil wires, that is, the proximal coil wire 10, a center coil wire 18, and the distal coil wire 11. The distal end portions of the proximal and the center coil wires 10, 18 are formed into the tapered portion 13 and a tapered portion 19, and the lengths L1 and L5 thereof are shorter than the lengths L2 and L6 of the portions of the proximal and the center coil wires 10, 18 except for the tapered portions 13, 19, respectively. The proximal end portions of the center and the distal coil wires 18, 11 are formed into the receiving end portions 20, 15, into which the respective tapered portions 13, 19 are inserted.

Figure 7:
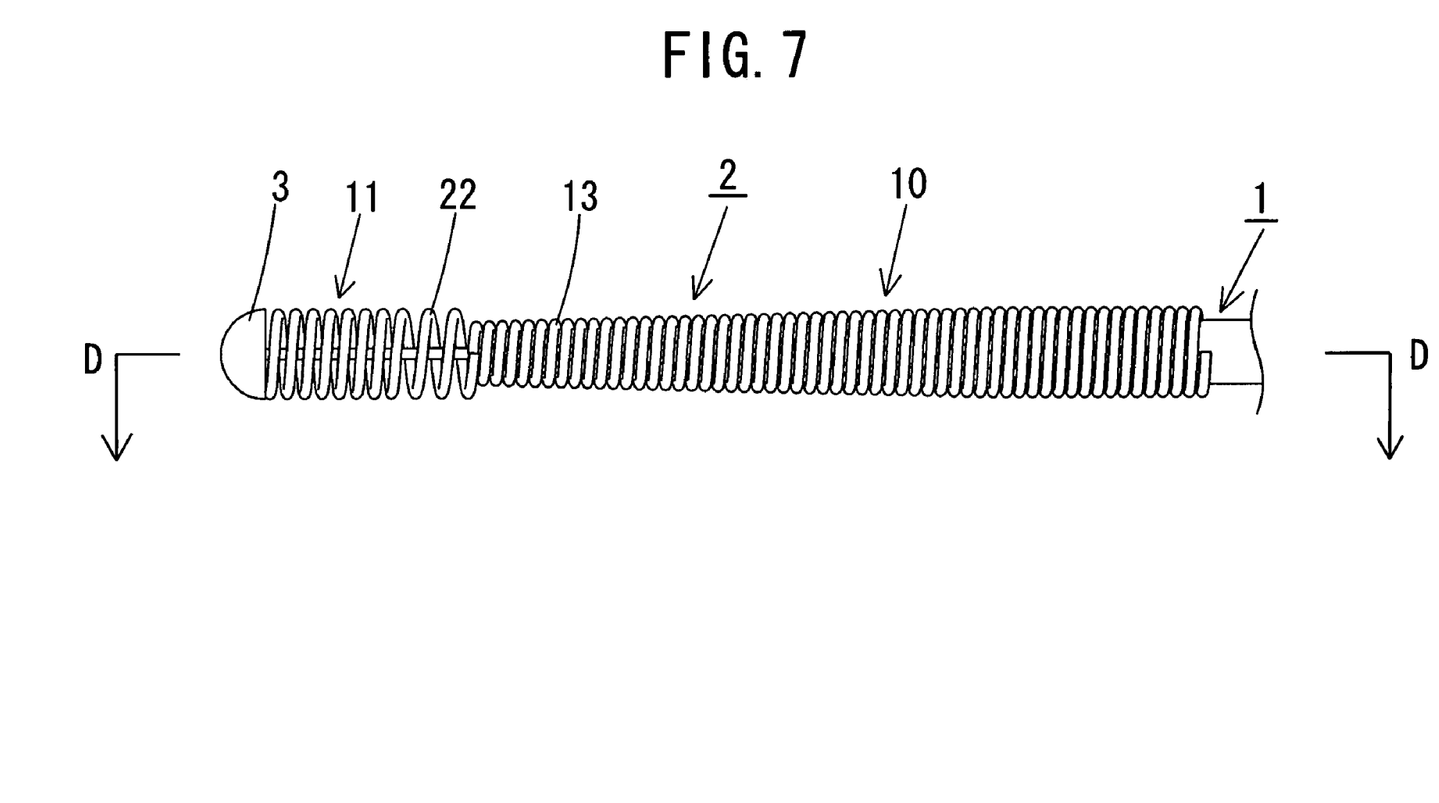
Figure 8:
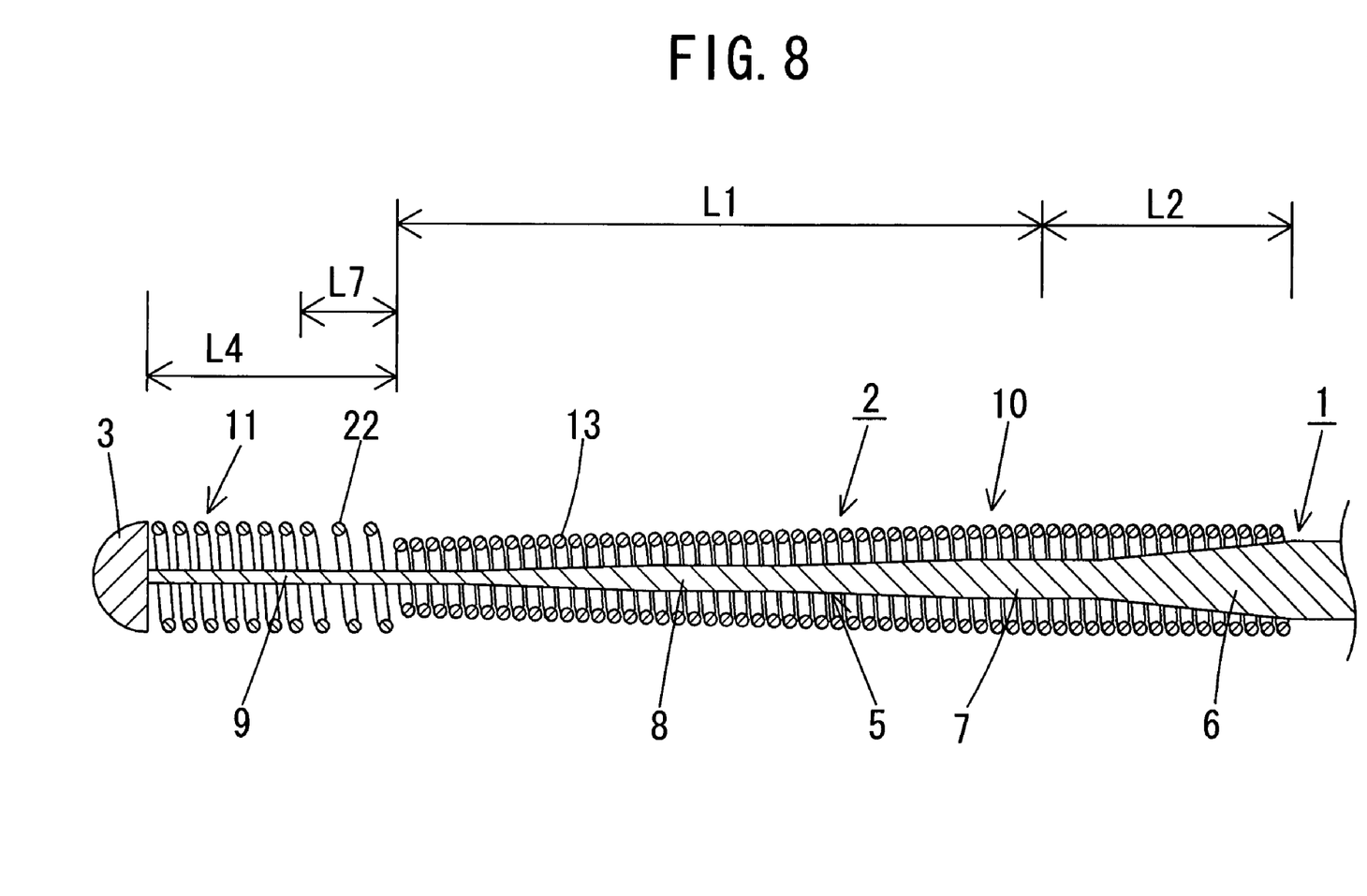
FIG. 8 is a cross-sectional view taken along line D-D of FIG. 7.

FIGS. 7 and 8 show a comparative example of, in which the proximal coil wire 10 and the distal coil wire 11 are formed integrally. The proximal portion of the distal coil wire 11 is formed into a wide-pitch portion 22, in which the pitches are larger than the remaining portion, and the length is indicated by a reference sign L7.

What is claimed is:
1. A guide wire comprising:
   (a) a core wire formed with a mounting portion at a distal end portion and having a distal end;
   (b) a plurality of coil wires being fitted onto the mounting portion substantially in tandem, and having different mechanical properties, adjacent coil wires being connected with each other at the corresponding ends thereof, said plurality of coil wires including a first coil wire having a distal end extending from the distal end of the core wire in the proximal direction of the guide wire and a second coil wire in tandem with the first coil wire and having a distal end positioned distally of a proximal end of the first coil wire, and (c) a distal end tip formed into a solid semi-spherical shape with its spherical surface being a distal end surface of the core wire and fixed to the respective distal ends of the core wire and said first coil wire, wherein one of the corresponding ends of adjacent coil wires is formed into a tapered portion gradually reducing in outer diameter toward said end, the other one of the corresponding ends is formed into a receiving end portion into which the tapered portion is inserted, the length of the insertion of the tapered portion into the receiving end portion is 2% to 40% of the whole length of the coil wire having the receiving end portion, and the pitches of the receiving end portion of the coil wire are formed to be larger than those of the remaining portion thereof.

2. A guide wire according to claim 1, wherein the mounting portion of the core wire comprises:

(a) a plurality of transitional portions continuously disposed in the axial direction, and reduced gradually in outer diameter toward the distal end; and (b) a distal end portion continuously disposed distally from the most distal transitional portion, and formed into a plate shape, wherein the taper ratio of the most proximal transitional portion is larger than that of other transitional portions.

3. A guide wire according to claim 1, wherein the coil wire positioned on the proximal side out of the adjacent coil wires is formed with a tapered portion.

4. A guide wire according to claim 1, wherein the most distal coil wire is formed of a radiopaque material.

* * * * *